(12) United States Patent
Mitchell et al.

(10) Patent No.: US 7,186,871 B2
(45) Date of Patent: Mar. 6, 2007

(54) PROCESS FOR ALKANE AROMATIZATION USING PLATINUM-ZEOLITE CATALYST

(75) Inventors: Scott F. Mitchell, The Woodlands, TX (US); Gopalakrishnan G. Juttu, Sugar Land, TX (US); Robert Scott Smith, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 10/748,418

(22) Filed: Dec. 30, 2003

(65) Prior Publication Data

US 2005/0143610 A1  Jun. 30, 2005

(51) Int. Cl.
*C07C 2/52* (2006.01)
(52) U.S. Cl. ..................... 585/418; 585/419
(58) Field of Classification Search ............... 585/418, 585/419
See application file for complete search history.

(56) References Cited

U.S. PATENT DOCUMENTS

| | | | |
|---|---|---|---|
| 3,756,942 A | 9/1973 | Cattanach | |
| 3,760,024 A | 9/1973 | Cattanach | |
| 4,766,265 A | 8/1988 | Desmond et al. | |
| 4,788,364 A | 11/1988 | Harandi | |
| 4,835,336 A | 5/1989 | McCullen | |
| 4,891,463 A * | 1/1990 | Chu | 585/415 |
| 5,672,796 A | 9/1997 | Froment et al. | |
| 5,827,422 A | 10/1998 | Drake et al. | |
| 6,017,442 A | 1/2000 | Wu et al. | |
| 6,160,191 A * | 12/2000 | Smith et al. | 585/475 |
| 6,593,503 B1 | 7/2003 | Wu et al. | |

OTHER PUBLICATIONS

"Ethane to Aromatic Hydrocarbons: Past, Present, Future", Anke Hagen and Frank Roessner, Catal. Rev.—Sci. Eng., vol. 42,(4), p. 403-437 (2000).
"Synthesis and Characterization of Ge-ZSM-5 Zeolites", Kosslick et al., J. Phys. Chem., vol. 97, p. 5678-5684 (1993).

* cited by examiner

*Primary Examiner*—Thuan Dinh Dang
(74) *Attorney, Agent, or Firm*—Jim Wheelington

(57) ABSTRACT

Aromatization of alkanes having one to four carbon atoms per molecule to aromatics, such as benzene, toluene and xylenes (BTX), uses a catalyst of a crystalline zeolite on which platinum has been deposited, specifically a platinum-containing ZSM-5. A byproduct of the process is a light gas fraction of methane and ethane. The use of a platinum-containing ZSM-5 catalyst in an alkane aromatization process, such as the Cyclar process, suppresses the formation of methane and increases selectivity to BTX. The high content of ethane relative to methane in the light gas fraction allows this process effluent to be a feedstream for a cracker.

15 Claims, No Drawings

PROCESS FOR ALKANE AROMATIZATION USING PLATINUM-ZEOLITE CATALYST

BACKGROUND OF THE INVENTION

1. Field of the Invention

This invention relates to aromatization of alkanes having one to four carbon atoms per molecule to aromatics, such as benzene, toluene and xylenes (BTX) using a catalyst including a crystalline zeolite, specifically a platinum-containing ZSM-5.

2. Description of the Prior Art

Aromatization is a well-known reaction wherein alkanes are converted to aryls. Aryls, such as benzene, toluene and xylene, can be commercially produced by catalytic reforming of petroleum naphtha. However, naphtha is in great demand for other petrochemical products, such as gasoline.

One example of an aromatization process which does not use naphtha as a feedstock is the Cyclar™ process which converts liquefied petroleum gas (LPG) directly into a liquid aromatics product in a single operation. LPG consists mainly of propane and butane but can also contain $C_2$, $C_5$ and $C_6$ alkanes and $C_2$–$C_6$ olefins. LPG, which is primarily recovered from gas and oil fields and petroleum refining operations, is relatively low in value and is available in abundance, qualities which make it a good feedstock for petrochemical applications, such as aromatization.

The Cyclar process is described as dehydrocyclodimerization, which is a sequential dehydrogenation of $C_3$ and/or $C_4$ alkanes to olefins, oligomerization of the olefins, cyclization to naphthenes and dehydrogenation of naphthenes to corresponding aromatics. Hydrocracking side reactions of the olefins and oligomers generate methane and ethane. The dehydrogenation reactions generate hydrogen. The typical catalyst used in this process is a gallium containing ZSM-5 zeolite.

U.S. Pat. No. 5,672,796 discloses a one stage process for aromatization of $C_3$–$C_6$ saturated hydrocarbons to a low methane-containing aromatic product using a partially-sulfided platinum/rhenium-containing crystalline aluminosilica molecular sieve catalyst with MFI crystal structure, preferably with a Si/Al ratio between 40 and 600.

U.S. Pat. No. 4,788,364 discloses a two stage process for dehydrocyclization and oligomerization-aromatization of $C_2$–$C_{10}$ paraffins to highly aromatic and olefinic gasoline using crystalline aluminosilicate catalysts, such as ZSM-5, which may incorporate phosphorus, gallium, tin, rhenium, zinc, platinum and copper. There were no examples in which these metals were incorporated into the catalyst and no disclosure of suppressing methane.

U.S. Pat. No. 4,835,336 discloses a process for converting nonaromatic $C_6$+ hydrocarbons to aromatics with a Pt/ZSM-5 catalyst which has been presulfided to increase aromatic selectivity and suppress hydrogenolysis, i.e., methane formation is passivated. There is no disclosure of use of such a catalyst, with or without presulfiding, with lower alkanes.

U.S. Pat. No. 4,766,265 discloses a catalyst for the conversion of ethane to liquid aromatic hydrocarbons. The catalyst is a zeolite-type alumino-, gallo- or boro-silicate (ZSM-5 or ZSM-11 being preferred) which has gallium, aluminum and/or zinc incorporated into the structure and has been treated with rhenium and a metal selected from nickel, palladium, platinum, rhodium and iridium, with platinum and rhodium being preferred. The second metal was believed to act as a promoter for the dehydrogenation reaction of the oligomerized intermediates formed from ethane which enhanced the overall selectivity to aromatics and decreased methane selectivity promoted by rhenium.

U.S. Pat. No. 3,756,942 discloses a process for the preparation of aromatic compounds from a feed of a mixture of paraffins, olefins and naphthenes with a ZSM-5 catalyst. The examples disclose a platinum-impregnated H-ZSM-5 catalyst which converted hexane to aromatics. Weight per cent of platinum varied from 0.04 to 0.35% and aromatic selectivity varied from 29 to 32.

U.S. Pat. No. 3,760,024 discloses a process for preparation of aromatic compounds from $C_2$–$C_4$ paraffins or olefins with a ZSM-5 type catalyst. A hydrogenation/dehydrogenation component, such as metals and oxides and sulfides of metals of Group VIB, Group IIB, Group VIIB and Group VIII, is not necessary but may be present.

U.S. Pat. No. 5,827,422 discloses a catalyst for converting a hydrocarbon or a hydrocarbon mixture to an olefin and a $C_6$ to $C_8$ aromatic hydrocarbon. The composition is an aluminosilicate of a silica, an alumina, and, optionally, platinum wherein the weight ratio of elemental aluminum to elemental silicon is in the range of from about 0.002:1 to about 0.25:1 and the weight ratio of the optimal platinum to silicon is in the range of from about 0.0005:1 to about 0.01:1. The hydrocarbon may be butane, isobutanes, pentane, isopentane, hexane, isohexane, cyclohexane, heptane, isoheptane, octane, isooctane, nonane, decane, undecane, dodecane, tridecane, tetradecane, pentadecane, hexadecane, butenes, isobutene, pentenes, hexenes, benzene, toluene, ethylbenzene, xylenes, and combinations of any two or more thereof and is preferably gasoline or a gasoline derivative.

U.S. Pat. No. 6,017,422 discloses a catalyst composition which is resistant to sulfur or a sulfur compound containing a zeolite, cerium or cerium oxide, and a Group VIII metal or metal oxide, such as platinum or platinum oxide, for converting hydrocarbons to $C_6$–$C_8$ aromatic hydrocarbons. The hydrocarbons may be those having 1 to about 30 carbon atoms, preferably aliphatic saturated hydrocarbons, such as ethane, propane, butane, pentane, hexane, heptane, octane, nonane, dodecane, gasoline, or combinations of two or more thereof. The zeolite is any commercially available zeolite which can catalyze the conversion of a hydrocarbon to an aromatic compound, but is preferably L zeolite. The examples disclose the advantages (higher feed conversion, higher benzene yield, and higher selectivity to benzene in the presence of a sulfur compound) of a Pt/Ce-promoted zeolite L catalyst over a Pt-promoted zeolite L catalyst (without Ce).

In the article "Ethane to Aromatic Hydrocarbons: Past, Present, Future" by Anke Hagen and Frank Roessner, Catal. Rev.—Sci. Eng., vol. 42(4), page 403–437 (2000) the introduction of platinum into a H-ZSM-5 led to a 1.5–2.0 fold increase of activity of ethane aromatization but selectivity to aromatics was relatively low.

U.S. Pat. No. 6,593,503 discloses platinum-promoted ZSM-5 zeolite, acid-treated and not acid-treated, for aromatization of hydrocarbons, preferably 4–25 carbon atoms and more preferably "gasoline-type" hydrocarbons, to $C_6$ to $C_8$ aromatics, such as benzene, toluene and xylenes. The examples demonstrated the benefit of acid treating to reduce the aluminum content in the zeolite.

Because of the acidity inherent to zeolites alkane cracking occurs in an alkane aromatization process which results in producing undesirable methane. It would be advantageous if methane production could be suppressed in favor of producing more ethane relative to methane from the side reactions of alkane aromatization generated could be used.

SUMMARY OF THE INVENTION

This invention concerns use of a platinum-containing ZSM-5 crystalline zeolite in the aromatization of alkanes having one to four carbon atoms per molecule to benzene, toluene and xylenes. The catalyst is synthesized by preparing a zeolite containing aluminum and silicon in the framework, depositing platinum on the zeolite and calcining the zeolite. The zeolite structure may be of MFI, FAU, TON, MFL, VPI, MEL, AEL, AFI, MWW or MOR, but preferably, the zeolite has a MFI structure, more preferably is ZSM-5 MFI zeolite. The catalyst is used in a process for aromatization of alkanes by contacting the zeolite on which platinum has been deposited with at least one alkane at aromatization conditions and recovering the aromatic product. A byproduct is a light gas fraction of hydrogen, methane and ethane. It is an attribute of the present invention that formation of methane is suppressed and that selectivity to ethane in the fuel gas is increased. The high content of ethane relative to methane in the light gas fraction, i.e., the mole fraction ratio of ethane relative to methane is in the range from 2 to 10, allows this process effluent to be a feedstream for a cracker.

DETAILED DESCRIPTION OF THE INVENTION

Depositing platinum on an aluminosilicate MFI zeolite catalyst precursor has been found to produce a catalyst for aromatization of alkanes having one to four carbon atoms per molecule that reduces the formation of methane relative to ethane and has relatively good selectivity for aromatics, e.g., benzene, toluene and xylene.

The zeolite can be prepared by any known method of preparing a MFI structure of aluminum and silicon. Zeolites are known to be crystalline aluminosilicates and include structures of $TO_4$ tetrahedra, which form a three dimensional network by sharing oxygen atoms where T represents tetravalent silicon and trivalent aluminum. Trivalent elements, such as gallium or boron may be substituted in any amount for the aluminum, i.e., in the range from 0 to 100%. Tetravalent elements, such as germanium, may be substituted in any amount for the silicon, i.e., in the range from 0 to 100%.

Zeolites generally crystallize from an aqueous gel. The typical technique for synthesizing zeolites comprises converting an amorphous silica to zeolite crystals by a hydrothermal process, employing a dissolution/recrystallization mechanism. The reaction medium may also contain structuring agents which are incorporated in the microporous space of the zeolite network during crystallization, thus controlling the construction of the network and assisting to stabilize the structure through the interactions with the zeolite components.

As disclosed in U.S. Pat. No. 3,702,886, hereby incorporated by reference, ZSM-5 zeolites may be produced by preparing a solution containing tetrapropyl ammonium hydroxide, sodium oxide, an oxide of aluminum or gallium, an oxide of silicon or germanium and water; heating the reaction mixture to a temperature of from about 100° C. to 175° C. for a period of time of from about six hours to 60 days, preferably 150 to 175° C. for 12 hours to 8 days; maintaining the mixture until crystals of zeolite are formed; cooling the reaction mixture to room temperature; and filtering, separating, washing and drying the crystals.

Methods of preparation of a MFI zeolite can also be found in J. Phys. Chem., vol. 97, p. 5678–5684 (1993), hereby incorporated by reference.

The silicon to aluminum atomic ratio (Si:Al) of the MFI zeolite is preferably greater than 2, more preferably in the range from 10 to 200, and most preferably in the range from 20 to 100.

Platinum is deposited on the MFI zeolite by any known method of depositing a metal on a zeolite. Typical methods of depositing a metal on zeolite are ion exchange and impregnation. Platinum is present preferably in the range from 0.05 to 5%, more preferably in the range from 0.1 to 2% and most preferably in the range from 0.2 to 1%.

The catalyst may be bound by oxides of magnesium, aluminum, titanium, zirconium, thorium, silicon, boron and mixtures thereof. Preferably, the binder is amorphous and is an oxide of aluminum (alumina) or silicon (silica).

One example of a zeolite within the present invention may have its chemical formula represented in IUPAC nomenclature as:

$[Pt_{0.0025}H^+][AlSi_{95}O_{192}]$-MFI

The invention is applicable to a variety of conversion processes which use catalysts to convert an alkane feed to aromatic products. In particular, the invention is applicable to hydrocarbon conversion processes, such as dehydrocyclization and conversion of light hydrocarbon to aromatics, e.g., Cyclar-type processing of a $C_3$ alkane to aromatics. These processes and the useful range of process conditions are all well known in the art. The CYCLAR (tradename) process is described in the paper "CYCLAR: One Step Processing of LPG to Aromatics and Hydrogen," by R. F. Anderson, J. A. Johnson and J. R. Mowry presented at the AIChE Spring National Meeting, Houston, Tex., Mar. 24–28, 1985. The dehydrocyclodimerization process increases carbon chain length by oligomerization, promotes cyclization, and dehydrogenates cyclics to their respective aromatics. The process operates at a temperature of about 350° C. to 650° C. and a relatively low pressure of about 10 to 2000 kPa gauge.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1 (Pt/ZSM-5)

15 g of a commercially available zeolite ZSM-5 (Zeolyst CBV 5514) of $SiO_2/Al_2O_3$=50 bound with alumina (50 wt % zeolite) were placed in an Erlenmeyer flask. 10 ml of 20 mM hydrogen hexachloroplatinate (IV) hydrate solution were added to the flask for incipient wetness of the bound zeolite. The contents of the flask were dried overnight at 90° C. and then calcined at 550° C. for five hours in a muffle furnace to form a catalyst. The catalyst was steamed at 550° C. for 16 hours.

COMPARATIVE EXAMPLE 1 (Re/ZSM-5)

3 g of a commercially available zeolite ZSM-5 (Zeolyst CBV 5514) of $SiO_2/Al_2O_3$=50 bound with alumina (50 wt % zeolite) were placed in a ceramic dish. 2.3 g of 54 mM ammonium perrhenate solution were added to the dish for incipient wetness of the bound zeolite. The contents of the dish were dried overnight at 90° C. and then calcined at 550° C. for five hours in a muffle furnace to form a catalyst. The catalyst was steamed at 550° C. for 16 hours.

COMPARATIVE EXAMPLE 2 (Au/ZSM-5)

The procedure of Comparative Example 1 was followed except 2.3 g of 2 mM gold (IV) chloride solution were used.

COMPARATIVE EXAMPLE 3 (Ru/ZSM-5)

The procedure of Comparative Example 1 was followed except 2.3 g of 1.5 wt % ruthenium (III) nitrosyl nitrate solution were used.

COMPARATIVE EXAMPLE 4 (Ru/ZSM5)

The procedure of Comparative Example 1 was followed except 3.89 g of zeolite ZSM-5 and 10 g of 11.3 wt % of zinc (II) nitrate solution were used.

COMPARATIVE EXAMPLE 5 (Fe/ZSM-5)

The procedure of Comparative Example 1 was followed except 6 g of zeolite ZSM-5 and 10 g of 14 wt % of iron (III) nitrate solution were used.

COMPARATIVE EXAMPLE 6 (ZSM-5)

Unmodified zeolite ZSM-5 ($SiO_2/Al_2O_3$) bound with alumina (50 wt % zeolite).

Reactor Conditions:

1 g of the catalyst diluted with 1 g of quartz chips was loaded into the reactor. The catalyst was reduced with a 40 ml/min flow of 50% $H_2$/50% $N_2$ for one hour. The gas flow was changed to 50% propane/50% $N_2$ over the catalyst with a reactor pressure of 10 psig and a reactor temperature of 520° C. The fuel gas composition of the product gas stream is shown below in Table 1.

TABLE 1

| Example | Metal | Fuel Gas (wt %) | $C_1$ (wt %) | $C_2$ (wt %) |
|---|---|---|---|---|
| 1 | Pt | 72.2 | 4.8 | 67.4 |
| Comp. 1 | Re | 37.5 | 11.08 | 26.38 |
| Comp. 2 | Au | 48.2 | 19.1 | 29.1 |
| Comp. 3 | Ru | 55.2 | 24.4 | 30.8 |
| Comp. 4 | Zn | 45.4 | 13.8 | 31.6 |
| Comp. 5 | Fe | 55.5 | 14.8 | 40.6 |
| Comp. 6 | — | 37.4 | 20.0 | 17.4 |

A series of catalyst were prepared using a commercial ZSM-5 zeolite and varying degrees of Pt loading as listed in Table 2 below.

EXAMPLES 2–5 (Cat #204-163, 164, 166 and 167)

10 g of a commercially available zeolite ZSM-5 (Zeolyst CBV 5514) of $SiO_2/Al_2O_3$=50 bound with alumina (50 wt % zeolite) were ion exchanged with 40 ml of $Pt(NH_3)_4(NO_3)_2$ solution of concentration as indicated in Table 2 for 24 h at 60° C. The solution was decanted the catalyst was rinsed with deionized water and dried overnight at 90° C. The catalyst was calcined in a muffle furnace with airflow at 300° C. for 4 hours.

TABLE 2

| Catalyst # | Concentration of Pt I.E. solution | Pt loading % | Reaction Temp ° C. | Conversion % | Fuel Gas % | C1 % | C2 % | BTX % |
|---|---|---|---|---|---|---|---|---|
| 204-163 | 0.002 M | 0.06 | 480 | 36.4 | 44.6 | 5.2 | 39.3 | 21.8 |
| 204-164 | 0.003 M | 0.09 | 480 | 44.7 | 52.8 | 3.2 | 49.7 | 16.1 |
| 204-166 | 0.004 M | 0.27 | 460 | 51.6 | 49.9 | 3.0 | 46.9 | 28.1 |
| 204-167 | 0.005 M | 0.33 | 470 | 46.9 | 35 | 3.3 | 31.7 | 44.0 |

Results for these catalysts demonstrate a correlation between Pt loading and selectivity to ethane. As can be seen from the data, as the Pt loading is lowered the selectivity to BTX lowers as well. The result is even more pronounced at the lowest Pt loading of 0.06 wt % where there is also a loss in catalyst activity as well. The Pt loading of the catalyst can be at about 0.1 wt % without loss of selectivity to ethane and about 0.3 wt % with little impact to conversion and selectivity to BTX.

The results above demonstrate the advantages of Pt/ZSM-5 as a catalyst for alkane aromatization. The fuel gas produced, when the Pt/ZSM-5 catalyst is used, has a higher content of ethane relative to methane.

An ethane-rich fuel gas would have greater benefit and more usefulness than a fuel gas which contains methane up to 50% by weight. Fuel gas which has methane as the major component would be useful primarily for its heat value, i.e., it would be burned. The ethane component could be separated out and used a feed for a cracker or converted to other products, such as ethylene or acetic acid; however, separation would be expensive and energy intensive. Fuel gas which has ethane as the majority component, i.e., greater than 50% by weight could be used for these other processes without separation.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for aromatization of alkanes comprising contacting an alkane having one to four carbon atoms per molecule with a catalyst under conditions to convert the alkane to benzene, toluene and xylenes and byproducts of methane and ethane wherein the catalyst consists essentially of platinum deposited on an MFI zeolite consisting of aluminum silicon, and oxygen in the framework.

2. The process of claim 1 wherein the catalyst has a silicon to aluminum atomic ratio (Si:Al) is greater than 2.

3. The process of claim 2 wherein the silicon to aluminum atomic ratio is in the range from 10 to 200.

4. The process of claim 3 wherein the silicon to aluminum atomic ratio is in the range from 20 to 100.

5. The process of claim 1 wherein the catalyst is Pt/ZSM-5 and the alkane is propane.

6. The process of claim 1 wherein platinum is present in the range from 0.06 wt % to 0.33 wt %.

7. The process of claim 1 wherein platinum is present in the range from 0.1 wt % to 0.3 wt %.

8. The process of claim 1 wherein the catalyst is bound by oxides of magnesium, aluminum, titanium, zirconium, thorium, silicon, boron or mixtures thereof.

9. The process of claim 1 wherein the catalyst has an amorphous support.

10. The process of claim 9 wherein the amorphous support is an oxide of aluminum (alumina) or silicon (silica).

11. The process of claim 1 wherein the chemical formula of the zeolite is represented as:

$[Pt_{0.0025}H^+][AlSi_{95}O_{192}]$-MFI.

12. The process of claim 1 wherein the process is a dehydrocyclodimerization process of a $C_3$ alkane to benzene, toluene and xylenes.

13. The process of claim 12 wherein the temperature is in the range of from 350° C. to 650° C.

14. The process of claim 12 wherein the pressure is in the range of from 10 to 2000 kPa gauge.

15. The process of claim 1 wherein the mole fraction ratio of ethane relative to methane is in the range from 2 to 10.

* * * * *